United States Patent
Wang

(10) Patent No.: US 7,700,780 B2
(45) Date of Patent: Apr. 20, 2010

(54) ZWITTERIONIC CHROMOPHORES AND MACROMOLECULES CONTAINING SUCH CHROMOPHORES

(75) Inventor: Zhi Yuan Wang, 3091 Applehill Drive, Ottawa, Ontario (CA) K1T 3Z2

(73) Assignee: Zhi Yuan Wang, Ottawa (CA)

( * ) Notice: Subject to any disclaimer, the term of this patent is extended or adjusted under 35 U.S.C. 154(b) by 1083 days.

(21) Appl. No.: 11/366,459

(22) Filed: Mar. 3, 2006

(65) Prior Publication Data

US 2006/0199951 A1    Sep. 7, 2006

Related U.S. Application Data

(60) Provisional application No. 60/658,162, filed on Mar. 4, 2005.

(51) Int. Cl.
| | |
|---|---|
| C07D 211/70 | (2006.01) |
| C07D 211/82 | (2006.01) |
| C07D 213/57 | (2006.01) |
| G01J 3/46 | (2006.01) |
| C09B 56/00 | (2006.01) |
| C08G 73/06 | (2006.01) |

(52) U.S. Cl. ............... 546/330; 546/1; 534/653; 528/391; 528/423; 528/495; 526/292.2; 356/402; 252/299.63

(58) Field of Classification Search ............ 528/423, 528/391, 495; 546/330, 1; 526/292.2; 252/299.63; 534/653; 356/402
See application file for complete search history.

(56) References Cited

U.S. PATENT DOCUMENTS 6,894,169 B1 *  5/2005  Wang et al. .................. 546/330

* cited by examiner

*Primary Examiner*—Duc Truong
(74) *Attorney, Agent, or Firm*—George A. Seaby

(57) ABSTRACT

The invention disclosed relates to functionalized zwitterionic chromophores of structural formula III and III'.

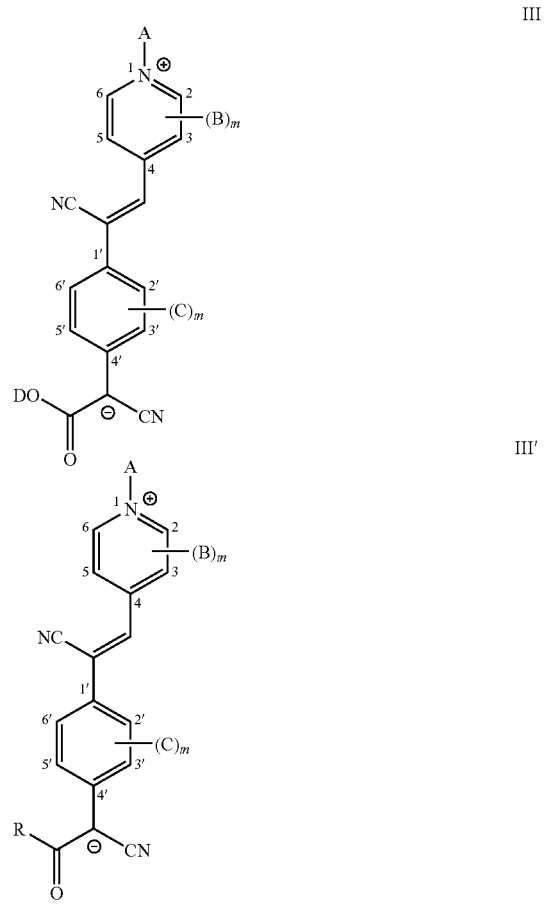

Wherein
  A is a linear or branched alkyl group having up to 20 carbon atoms and the desired functional groups,
  B is hydrogen, alkyl, aryl, halo, heterocyclic, alkoxy or nitro groups at 2, 3, 5 or 6 positions on the pyridine ring,
  C is hydrogen, aryl or a linear or branched alkyl group at 2', 3', 5' or 6' positions on the benzene ring, which has up to 70 carbon atoms and contains the desired functional group,
  D is a linear or branched alkyl, aryl or substituted aryl group, which has up to 70 carbon atoms and contains the desired functional group,
  R is C1-C4 alkyl or aryl, and
  m is an integer of from 0 to 4.

29 Claims, No Drawings

ZWITTERIONIC CHROMOPHORES AND MACROMOLECULES CONTAINING SUCH CHROMOPHORES

This application claims benefit of U.S. Provisional Application 60/658,162 filed Mar. 4, 2005.

FIELD OF THE INVENTION

This invention relates to functionalized zwitterionic chromophores, and macromolecules including such chromophores, and methods for making them.

BACKGROUND OF THE INVENTION

Second-order nonlinear optical (NLO) chromophores and polymers are being actively pursued for applications in high-speed electro-optic (EO) modulators, and other integrated optoelectronic and microwave devices [(a) Kajzar, F.; Lee, K.-S.; Jen, A. K.-Y. Adv. Polym. Sci. 2003, 161, 1. (b) Dalton, L. Adv. Polym. Sci. 2002, 158, 1.] Since the EO effect is not a naturally occurring property in polymers, the poling under an electrical field is needed to induce the linear EO coefficient, which is parallel to an applied field as given by:

$$\chi_{zzz}^{(2)} = N\beta_{111} f_\omega^2 f_0^2 \mu E/5kT$$

where N is the density of NLO chromophore, $\beta_{111}$ is the first hyperpolarizability of the molecular chromophore in the direction of $\mu$, $f_\omega^2$ and $f_0^2$ are local field correction factors at frequencies $\omega$ and zero respectively, $\mu$ is the ground state dipole moment of the chromophore, E is the applied electric field and T is the temperature. Simple translation of these molecular values into bulk property values assumes that all the molecules represented in the number density (N), respond to the local poling field (E) at a temperature (T). The electro-optic coefficient ($r_{33}$) can be given as:

$$r_{33} \approx 2/n^4 N f_0^2 \beta \langle \cos^3\theta \rangle$$

To be practically used in high-performance or new EO devices, NLO polymeric materials should have large and stable EO response or $r_{33}$ values, for example, much larger than that ($r_{33}=31$ pm/V) of LiNbO$_3$ crystals currently used in commercial EO modulators, at the wavelengths of 1310 nm, 1485-1525 nm, 1525-1562 nm and 1565-1620 nm, as prescribed by the International Telecommunications Union. Furthermore, it is desirable to maximize N and the product of dipole moment ($\mu$) and molecular hyperpolarizability ($\beta$) or $\mu\beta$. The former factor (N) is determined by the number of active NLO chromophores in the polymer and the latter ($\mu\beta$) is a property of the chromophore. Accordingly, ideal chromophores for EO applications should have large hyperpolarizability ($\beta$) such as those having extended $\pi$-conjugated systems or large dipole moment ($\mu$) or both, and should be readily soluble in solvents and polymer matrices. However, extended conjugation in molecules tends to lead to poor thermal and photochemical stability. The large dipole moment is likely to cause strong dipole-dipole interaction between chromophores, which is a result of stacking the two chromophores in a head-to-tail fashion. Thus, such a dipole interaction can lead to the diminished dipole orientation or even completely cancellation of dipole orientation of chromophores during the poling process, which gives rise to low or no EO response.

Equally importantly, suitable NLO materials must be able to be formulated and standardized to fulfil the processing requirement for device development and fabrication. For most developmental work on EO devices [(a) Shi, Y.; Zhang, C.; Zhang, H.; Bechtel, J. H.; Dalton, L. R.; Robinson, B. H.; Steier, W. H. Science 2000, 288, 119. (b) Lee, M.; Katz, H. E.; Erben, C.; Gill, D. M.; Gopalan, P.; Heber, J. D.; McGee, D. J. Science 2002, 298, 1401. (c) Paloczi, G. T.; Huang, Y.; Yariv, A.; Luo, J.; Jen, A. K.-Y. Appl. Phys. Lett. 2004, 85, 1662.], the guest-host type of NLO materials are routinely employed. However, phase separation over time and poor temporal stability of the poled NLO materials are common as reported in literature, due to poor solubility and facile dipole relaxation of chromophores in a non-crosslinked polymer matrix. Linking the chromophores via covalent bonds onto linear or hyperbranched macromolecules, which include oligomers and polymers in any molecular weights, can effectively increase the chromophore loading, prevent phase separation and stabilize the dipole orientation [(a) Burland, D. M.; Miller, R. D.; Walsh, C. A. Chem. Rev. 1994, 94, 31. (b) Bai, Y.; Song, N.; Gao, J. P.; Sun, X.; Wang, X.; Yu, G.; Wang, Z. Y. J. Am. Chem. Soc. 2005, 127, 2060.]. However, chromophores must be properly functionalized for incorporation into linear and hyperbranched macromolecules by grafting or polymerization.

A large number of chromophores have been synthesized and some exhibit very large macroscopic nonlinearities in guest/host polymers and grafted polymers. A strong 'push-pull' molecule with both electron accepting and electron donating groups linked by a conjugated moiety usually shows a finite P value. For example, chromophore-1 reported by Dalton et al (Opt. Lett, 1998, 23, 478) is a neutral molecule with relatively small dipole moment and contains several double bonds; DEMI reported by Szablewski et al (J. Am. Chem. Soc. 1997, 119, 3144) is a charged molecule or zwitterionic and has just one bridging double bond and fairly large dipole moment (e.g., 45 D). Zwitterionic chromophores are promising as NLO molecules, because their strongly asymmetric conjugated structures result in both a large hyperpolarizability and dipole moment. They are also deemed to be more stable than the neutral chromophores, due to less labile double bonds. The aligned or poled zwitterionic chromophores in a polymer are calculated to have extremely high EO coefficients ($r_{33}>210$ pm/V, Cross, G. et al. Opt. Mater. 2002, 21, 29.). To unlock the potential of the class of zwitterionic chromophores for EO device applications, one must find a way to effectively reduce the dipole-dipole interaction.

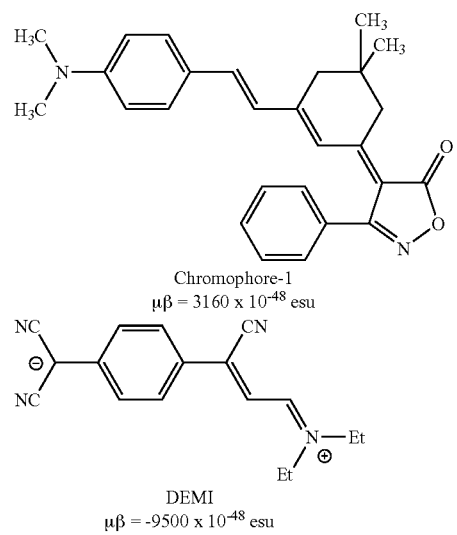

Chromophore-1
$\mu\beta = 3160 \times 10^{-48}$ esu

DEMI
$\mu\beta = -9500 \times 10^{-48}$ esu

Some zwitterionic chromophores structurally similar to DEMI but containing the pyridinium moiety and the hydroxy groups have been disclosed (Wang, Z. Y., et al. U.S. Pat. No. 6,894,169). These PQDM chromophores have the formulae:

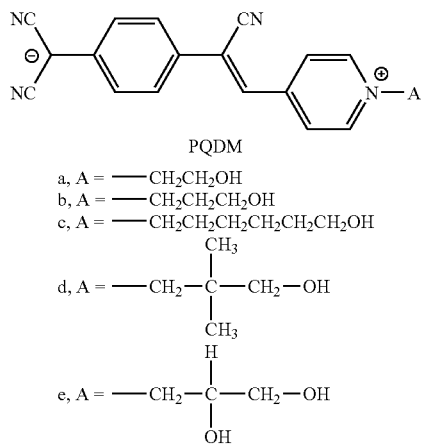

PQDM
a, A = —CH$_2$CH$_2$OH
b, A = —CH$_2$CH$_2$CH$_2$OH
c, A = —CH$_2$CH$_2$CH$_2$CH$_2$CH$_2$CH$_2$OH
d, A = —CH$_2$—C(CH$_3$)(CH$_3$)—CH$_2$—OH
e, A = —CH$_2$—C(H)(OH)—CH$_2$—OH

DEMI and PQDM have large dipole moments and large β values. But they also show poor solubility and strong dipole-dipole interaction. As a result, only a very small amount (1-3 wt %) of each chromophore could be doped into a host polymer without severe phase separation. The hydroxy-containing PQDM can be introduced into a host polymer via a covalent bond, but when PQDM chromophores in the polymer are more than 10 wt %, the EO coefficients drop due to increased dipole-dipole interaction. PQDM chromophores lack of proper substituents at the pyridinium and phenylene units to allow for reduction of the dipole-dipole interaction. None of three cyano groups could be further chemically modified or converted into other functional groups, such as an ester group, by any known chemical transformations without chemically damaging the other parts of the PQDM molecules. The disclosed PQDM chromophores have not reached and will not reach the high EO coefficients as expected for this class of zwitterionic NLO chromophores.

SUMMARY OF THE INVENTION

Thus, according to the invention applicant has introduced a functional group into zwitterionic chromophores, which can serve as electron withdrawing groups and as a handle to link other groups with desired features. The desired features may include a large bulky group to impart the solubility and to reduce the dipole-dipole interaction and a reactive group for incorporation of such a chromophore into a host polymer or macromolecule or crosslink therein.

Also, according to the invention, applicant provides a zwitterionic chromophore with proper functional groups that are able to be converted into macromolecular chromophores, such as linear and hyperbranched macromolecules, for easy formulation of NLO materials, better purification and improved solubility.

Further, according to the invention, Applicant introduces substituents into the skeleton, ideally the middle part, of the chromophore molecule, for the purpose of reduction of the dipole-dipole interaction between chromophores.

Yet further, the present invention provides generally a new type of zwitterionic chromophore that contains several different functional groups and substituents, which permit it to be grafted onto a host polymer and to be polymerized or copolymerized to form linear or hyperbranched macromolecules, and methods of making such a chromophore. The invention also provides generally a new type of NLO macromolecules containing a high content of the said chromophore and showing a good solubility in organic solvents and good compatibility with a variety of conventional host polymers. The invention further provides generally a new type of NLO polymer blends that are formulated by mixing the said chromophores or chromophore-containing macromolecules with a variety of conventional host polymers. Furthermore, the invention provides generally the use of the inventive chromophores and corresponding macromolecules and blends as NLO materials in a device showing useful EO response after thermal poling under the electrical field.

It is a significant feature of this invention that various electron-withdrawing groups, comparable to the cyano group, and also act as a handle for the introduction of the other functional groups, are provided. Such electron withdrawing groups include an ester group, a keto group, a sulfone (—SO$_2$R or —SO$_2$Ar), —NO$_2$ and extended acceptors with C═C or phenylene or thiophene inserted between the NC—CH and the ester, keto and sulfone groups.

Yet another feature of this invention is that the ester group can impart the solubility to the said chromophore and prevent the chromophores from close stacking, which leads to the diminished dipole-dipole interaction, due to the ester's more flexible and larger size than the cyano group.

Another feature of this invention is that the said zwitterionic chromophores are favourably formed, with the desired stronger electron acceptor CN at the ethylene bridge. Subsequently, the observed exceptionally high hyperpolarizability for the chromophores disclosed herein can be attributed to this unusual reaction and unique chemical structures of chromophores as shown in formula III and III'.

DETAILED DESCRIPTION OF THE INVENTION

According to the invention, the process for making the said chromophores involves the use of a picolinium salt (I) and compound II. Picolinium halides (I) are prepared by reacting the halide of an organic compound having a desired functional group with 4-picoline and substituted 4-picolines. This produces a picolinium halide having the desired functional group with or without the substituents on the pyridine ring. It has the general formula I, as follows:

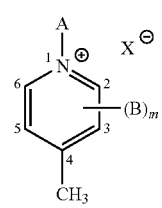

I where A is a linear or branched alkyl, aryl or substituted aryl group having up to 30 carbon atoms and the desired functional groups, and X is Cl, Br, I, tosylate or mesylate and is preferably Br or I. Examples of functional groups are —OH (hydroxy or phenolic), —C≡CH, and —N$_3$. Examples of alkyl groups are those having 2 to 8 carbon atoms.

The substituent B is hydrogen, alkyl, aryl, halo, heterocyclic, alkoxy or nitro groups at 2, 3, 5 or 6 positions on the pyridine ring and m is an integer of from 0 to 4. In one embodiment, B is hydrogen at 2,3,5 and 6 positions, and as well alkyl containing 1 to 6 carbon atoms, chloro, bromo, methoxy, phenyl and substituted pyridyl group at any of 2,3,5 and 6 positions.

The following picolinium salts (designated herein as compounds Ia-Ig) were prepared, according to the method disclosed in U.S. Pat. No. 6,894,169, the disclosure of which is incorporated herein by reference.

Ia-g

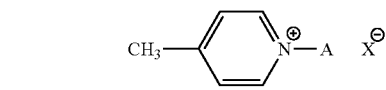

X = Br or I
a, A = ―CH$_2$CH$_2$OH
b, A = n-hexyl
c, A = benzyl

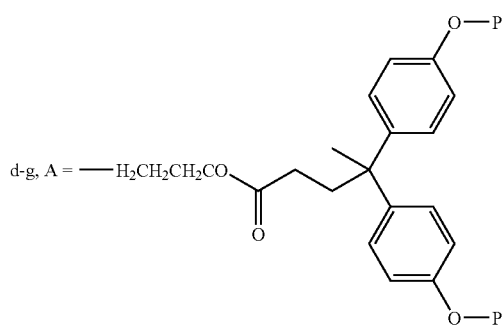

d-g, A = ―H$_2$CH$_2$CH$_2$CO d, P = H
e, P = ―CH$_2$―≡
f, P = ―C(O)―CH$_2$―N$_3$

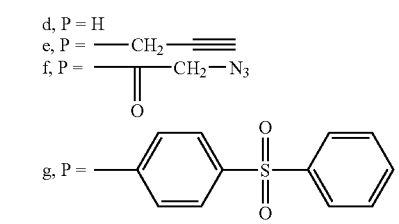

g, P =

In addition, the following substituted picolinium salts Ih-In were prepared as examples.

Ih-n

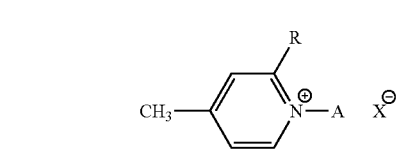

X = Br or I
h, R = CH$_3$, A = n-hexyl
i, R = CH$_3$, A = ―CH$_2$CH$_2$CH$_2$OH

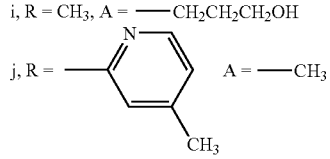

j, R = , A = ―CH$_3$

-continued

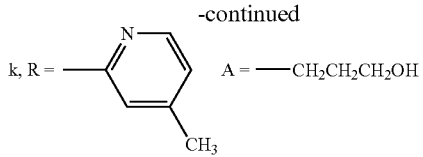

k, R = , A = ―CH$_2$CH$_2$CH$_2$OH l, m, n:

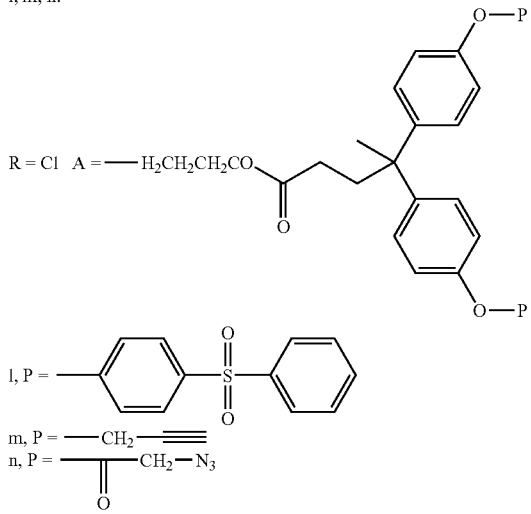

R = Cl   A = ―H$_2$CH$_2$CH$_2$CO l, P = ―C$_6$H$_4$―S(O)$_2$―C$_6$H$_5$ m, P = ―CH$_2$―≡
n, P = ―C(O)―CH$_2$―N$_3$

According to the invention, compounds II are prepared according to the known method (Iwatsuki, S.; Itoh, T.; Iwai, T.; Sawada, H. *Macromolecules* 1985, 18, 2726.) as shown in the reaction scheme below. This 2-step synthetic process produces a series of compounds having the desired substituent C on the benzene ring and the electron-withdrawing group containing D, with the general formula II:

II

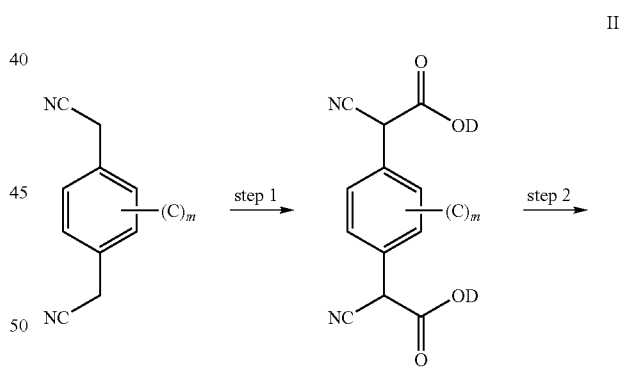

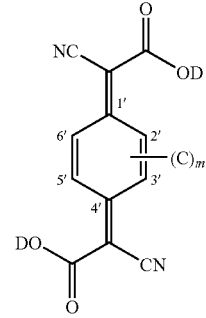

where the substituent C is hydrogen, aryl or a linear or branched alkyl group at 2', 3', 5' or 6' positions on the benzene ring, which has up to 70 carbon atoms and contains the desired functional group. The aryl groups can be phenyl or substituted phenyl. The letter m is an integer of from 0 to 4. In one embodiment of the invention, the substituent C is hydrogen at 2', 3', 5' and 6' positions, phenyl at 2' and 5' positions, and 2-ethylcarboxylate (—CH$_2$CH$_2$COOR) at 2' and 5' positions, in which R is alkyl and aryl having up to 50 carbon atoms with or without the presence of the functional group. In some embodiments of the invention, the desired functional group present in C is —OH (hydroxy or phenolic), —C≡CH and —N$_3$.

Uniquely, the group containing D, e.g. an ester group, serves as an electron-withdrawing group comparable to the cyano group and a handle to introduce the functional groups. Furthermore, this electron-withdrawing group can impart the solubility to the said chromophore and prevent the chromophores from close stacking, which leads to the diminished dipole-dipole interaction, due to its more flexible and larger size than the cyano group. Other electron-withdrawing groups include a keto group, a sulfone (—SO$_2$R or —SO$_2$Ar), —NO$_2$ and extended acceptors with C=C or phenylene or thiophene inserted between the NC—CH and the ester, keto and sulfone groups. Accordingly, D is a linear or branched alkyl, aryl or substituted aryl group, which has up to 70 carbon atoms and contains the desired functional group. In some embodiments of the invention, D is methyl, ethyl, 2-hydroxyethyl (—CH$_2$CH$_2$OH) and the derivatives of 2-hydroxyethyl (—CH$_2$CH$_2$OR), in which R is alkyl and alkoxycarbonyl having up to 50 carbon atoms with or without the presence of the functional group. If desired, the functional group present in R is —OH (hydroxy or phenolic), —C≡CH and —N$_3$.

As an example, the following bis(alkoxycarbonyl)-7,8-dicyanoquinodimethines (designated herein as compounds IIa-IIe) are prepared.

IIa–e

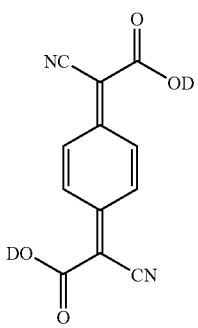

a, D = ——CH$_3$
b, D = ——CH$_2$CH$_2$OH
c, D = ——CH$_2$—C≡CH
d, D = ——CH$_2$CH$_2$OCOCH$_2$N$_3$

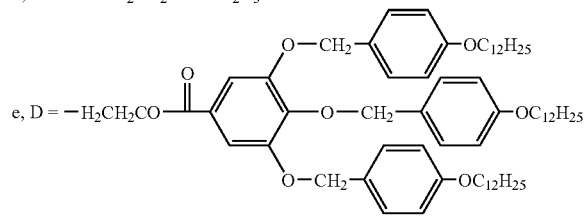

e, D = —H$_2$CH$_2$CO—

In addition, compounds IIf-IIi are prepared by using the substituted α,α-dicyano-p-xylenes, which can be readily synthesized by the Ni-catalyzed coupling reactions of 2,5-dibromo-α,α-dicyano-p-xylene or its precursor, 2,5-dibromo-p-xylene, with a variety of acrylates (Lebedev, S. A.; Lopatina, V. S.; Petrov, E. S.; Beletskaya, I. P. *J. Organomet. Chem.* 1998, 344, 253). In this series, R within the substituent —CH$_2$CH$_2$CO$_2$R is alkyl having the carbon atoms ranging from 1 to 16 and typically derived from commercially available and synthetically known acrylates, such as methyl, etheyl, n-butyl, phenyl and 2-hydroxyethyl, t-butyl, 1-adamantyl, 2-norbornanemethyl and propargyl acryaltes. R is also the derivative of the 2-hydroxyethyl moiety, which is alkyl and alkoxycarbonyl having up to 50 carbon atoms with or without the presence of the functional group. Thus, many more bis (alkoxycarbonyl)-7,8-dicyanoquinodimethines II can be realized and synthesized IIf-j

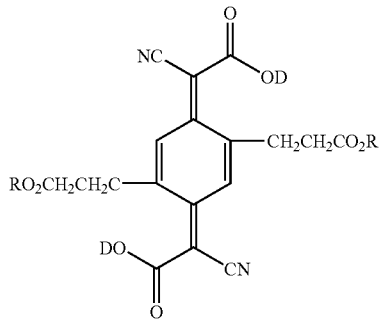

f, D = ——CH$_3$
g, D = ——CH$_2$CH$_2$OH
h, D = ——CH$_2$—C≡CH
i, D = ——CH$_2$CH$_2$OCOCH$_2$N$_3$

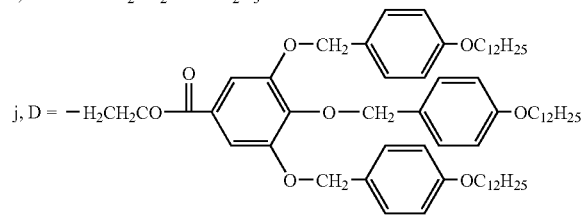

j, D = —H$_2$CH$_2$CO— with combination of different R and D groups.

II-k

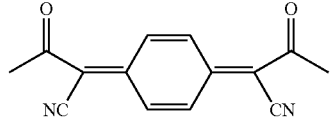

II-l

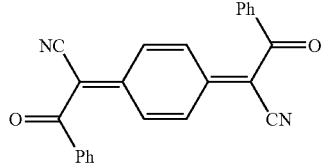

7,8-diacetyl-7,8-dicyanoquinodimethine (II-k), 7,8-dibenzoyl-7,8-dicyanoquinodimethine (II-l) were synthesized according the literature methods [Iwatsuki, S.; Itoh, T.; Sato, T.; Higuchi, T. *Macromolecules* 1987, 20, 2651.].

7,8-diacetyl-7,8-dicyanoquinodimethine: IR (KBr, cm$^{-1}$): 2205 ($v_{C≡N}$), 1676 ($v_{c=o}$).

7,8-dibenzoyl-7,8-dicyanoquinodimethane: IR (KBr, cm$^{-1}$): 2198 ($v_{C≡N}$), 1659 ($v_{c=o}$).

Furthermore, compounds II-m are prepared by using the phenyl substituted α,α-dicyano-p-xylenes, which can be readily synthesized from 2,5-dibromo-α,α-dicyano-p-xylene or its precursor, 2,5-dibromo-p-xylene.

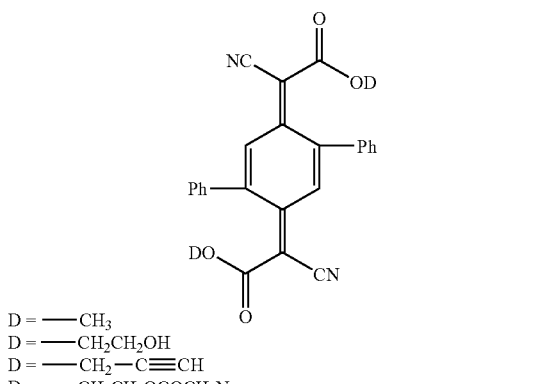

D = —CH₃
D = —CH₂CH₂OH
D = —CH₂—C≡CH
D = —CH₂CH₂OCOCH₂N₃

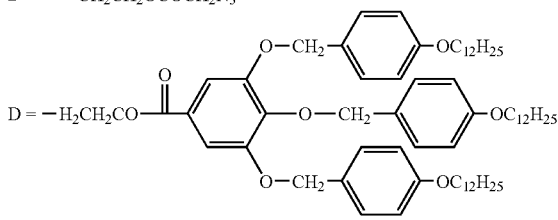

According to the invention, when a picolinium salt (I) is reacted with a compound (II), a zwitterionic chromophore is surprisingly formed as a major product in good yields, which has the general formula III and III', as follows:

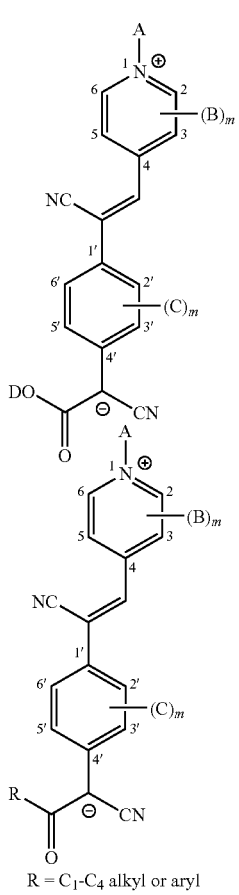

Where A, B, C and D are retained from the starting reactants I and II. By cross-coupling of I and II, a variety of chromophores III and III' can be realized and prepared under the similar, general reaction conditions. As representatives of all the possible chromophores with the formula III and III', the following chromophores IIIa-IIIe are obtained under the similar reaction conditions and characterized for their structures, thermal stability, and linear absorption and nonlinear optical properties (Table 1). The β values are among the highest values ever reported to date for all the known chromophores and also the same or very close to those for PQDM chromophores. This demonstrates the ability of the ester group as a good electron-withdrawing group.

TABLE 1

IIIa: D = CH₃, A = n-hexyl

IIIb: D = CH₃, A = —H₂CH₂CH₂CO...

IIIc: D = CH₃, A = CH₂CH₂OH

IIId: D = CH₃, A = benzyl

IIIe: D = CH₂CH₂OH, A = benzyl

Characterizations of representative zwitterionic chromophores

| Chromophore | λ_max (DMF) | ε(×10⁴) Lcm⁻¹mol⁻¹ | Td (TGA) 5% wt loss | β at 1.07 μm |
|---|---|---|---|---|
| IIIa | 674 nm | 1.6500 | 228° C. | 1700 × 10⁻³⁰ esu |
| IIIb | 677 nm | 3.0446 | 234° C. | 1660 × 10⁻³⁰ esu |
| IIIc | 668 nm | 3.7885 | 215° C. | 1729 × 10⁻³⁰ esu |
| IIId | 691 nm | 3.1251 | 250° C. | 1797 × 10⁻³⁰ esu |
| IIIe | 660 nm | 3.050 | 235° C. | 1710 × 10⁻³⁰ esu |

Td: onset temperature for 5% weight loss in nitrogen, as assessed by thermogravimetry (TGA). Hyperpolarizability (β) is obtained from the Hyper-Rayleigh scattering measurement at 1.07 μm wavelength.

Under the similar conditions, by reacting a picolinium salt (I) with compounds II-m the zwitterionic chromophores III' containing the substituted aryl groups on the central benzene ring, such as III'-a and III'-b, are obtained.

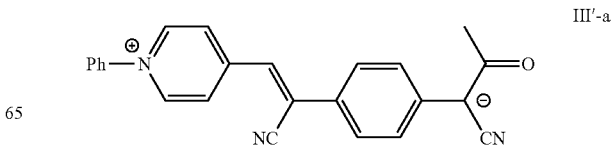

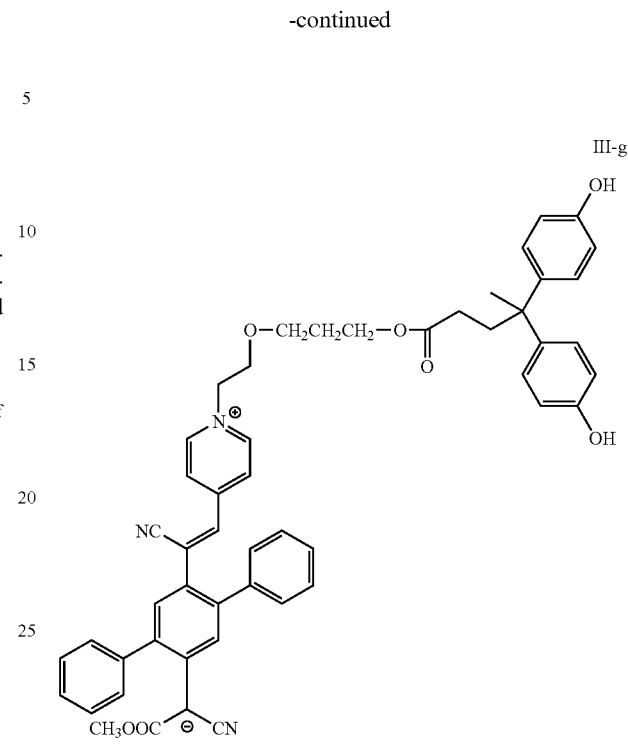

III'-b

Furthermore, by reacting a picolinium salt (I) with compounds II-k and II-l, the zwitterionic chromophores III containing a keto electron-withdrawing groups, such as III-f and III-g, are obtained.

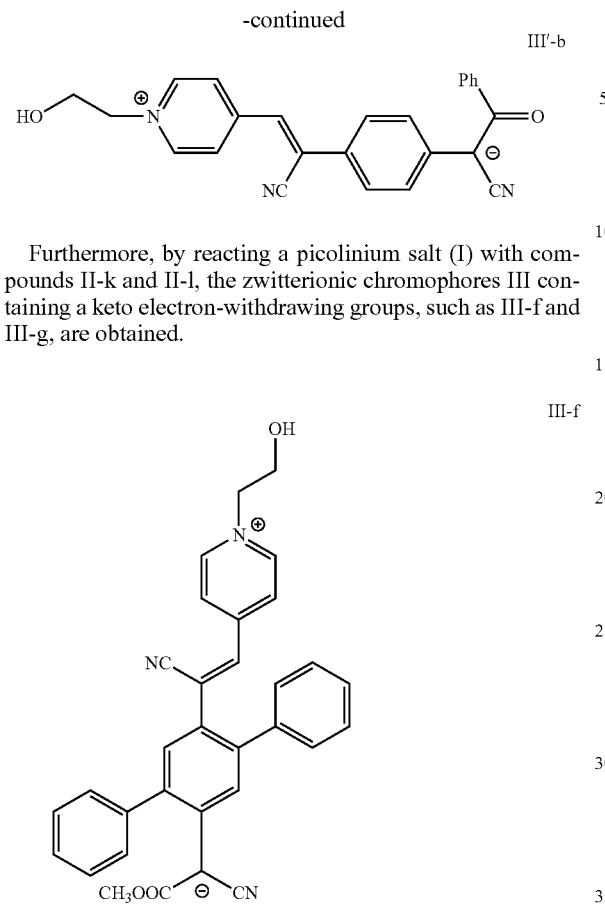

III-f

III-g

Alternatively, chromophores III and III' can be derived from another chromophores. For example, chromophore III-h is obtained by esterification of chromophore III-c.

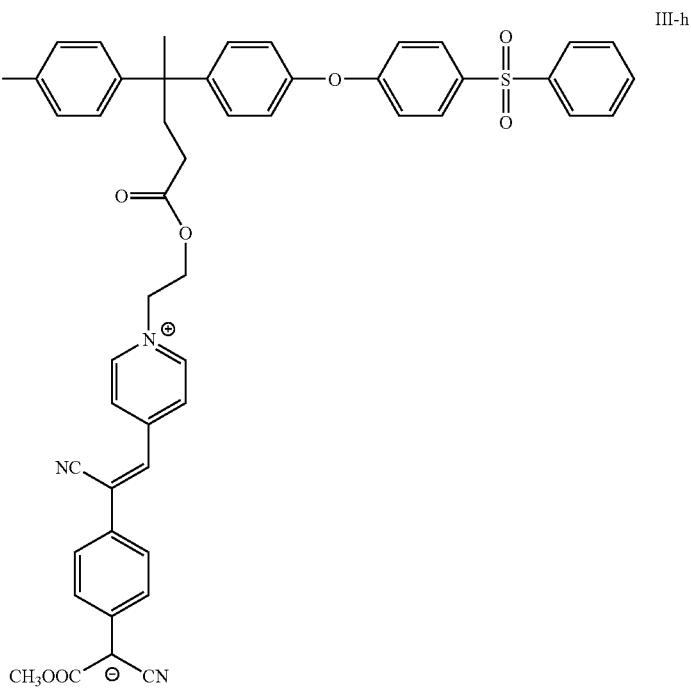

III-h

The solubility of the said chromophores is significantly improved, in comparison with the previously disclosed PQDM chromophores. For example, IIIb is readily soluble in DMF, DMAc, NMP, DMSO, THF and dioxane. Furthermore, chromophores bearing large ester groups such as those derived from IIe and IIh were found even more soluble in above solvents and other common organic solvents, such as chloroform, dichrolobenzene, tetracholorethane and even acetonitrile and acetone. High solubility is an advantage in this case, as more chromophores can be doped into a host polymer and the dipole-dipole interaction is likely to be diminished.

Besides the spectroscopic characterizations, the x-ray structure of the single crystals of IIId further confirms the structure of this type of zwitterionic chromophores (see below). Although the x-ray analysis indicates one particular alkenyl isomer that is likely to be the major product for all the chromophores III and III', it is still possible that the isolated product is a mixture of both cis- and trans-isomers, although in a different ratio, and the observed hyperpolarizability of the chromophores and the EO coefficients for the poled polymer films are contributed by either or both isomeric products.

mixed therewith in an amount of 1-30% by weight. The host can be any oligomer or polymer, termed macromolecules, which have good solubility in an organic solvent and has complementary functional groups to those of the chromophores.

The chromophores are grafted onto the host macromolecules by reacting their functional groups with the complementary functional groups of the host. The grafting reaction of the novel chromophores onto a host polymer with a complementary functional group using a coupling agent leads to the formation of the said chromophore-grafted polymers. In one embodiment of the invention, the chromophore has a hydroxyl group, and the complementary group (e.g., carboxylic acid) be present on the polymer, to form a covalent ester bond. Thus, chromophore III-c was grafted onto the acid-containing poly(ether sulfone) by using a coupling agent 1-[3-(dimethylamino)propyl]-3-ethylcarbodiimide (EDC).

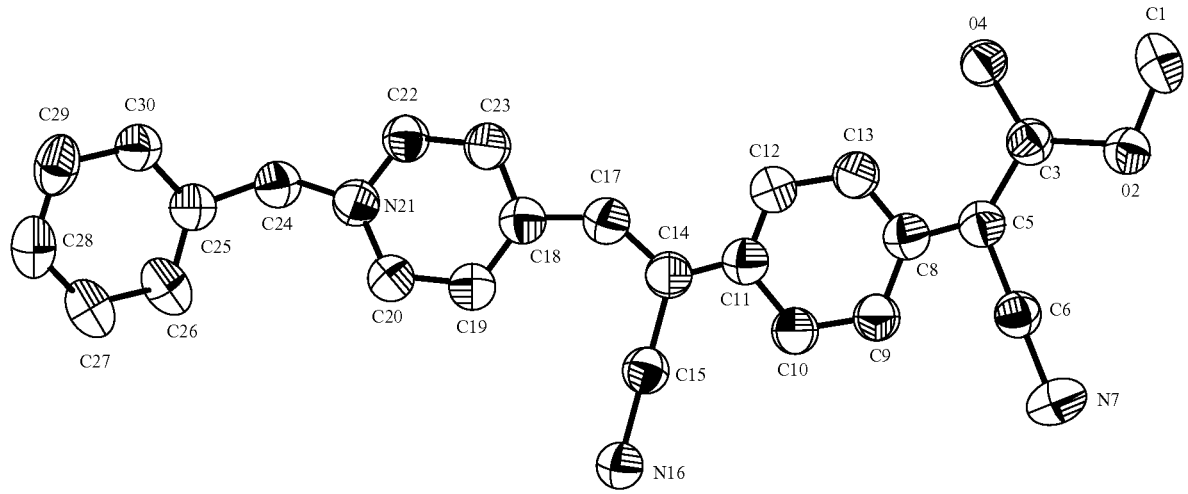

According to the reaction mechanism (Weir, C. A. M.; Hadizad, T.; Beaudin, A. M. R.; Wang, Z. Y. *Tetrahedron Lett.* 2003, 44, 4697.) and general understanding about common nucleophilic displacement reactions, the reaction of I and II would have been expected to yield the chromophores with the ester (—$CO_2D$), rather than CN, at the bridging ethylene unit, since the CN group is deemed to be a better leaving group. However, for an unknown reaction mechanism, zwitterionic chromophores III and III' are favourably formed, with the desired stronger electron-withdrawing CN at the ethylene bridge. Subsequently, the observed exceptionally high hyperpolarizability for the chromophores disclosed herein can be attributed to this unusual reaction and unique chemical structures of chromophores as shown in formula III and III'.

The invention also includes macromolecules including the inventive chromophores either covalently linked thereto or

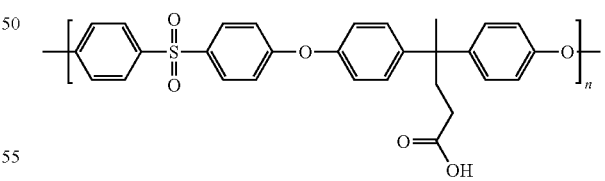

If desired, some of the complementary functional groups on the polymer can be used to react with non-chromophores, which have the same functional group as the chromophores. The non-chromophores can be inert or reactive groups. The later can be crosslinkers that react upon heating or irradiation to crosslink the polymer. In one embodiment of the invention, the non-chromophores used are methanol as an inert group and 5-aminobenzocyclobutenone as a crosslinker, which are present in polymer IV-a.

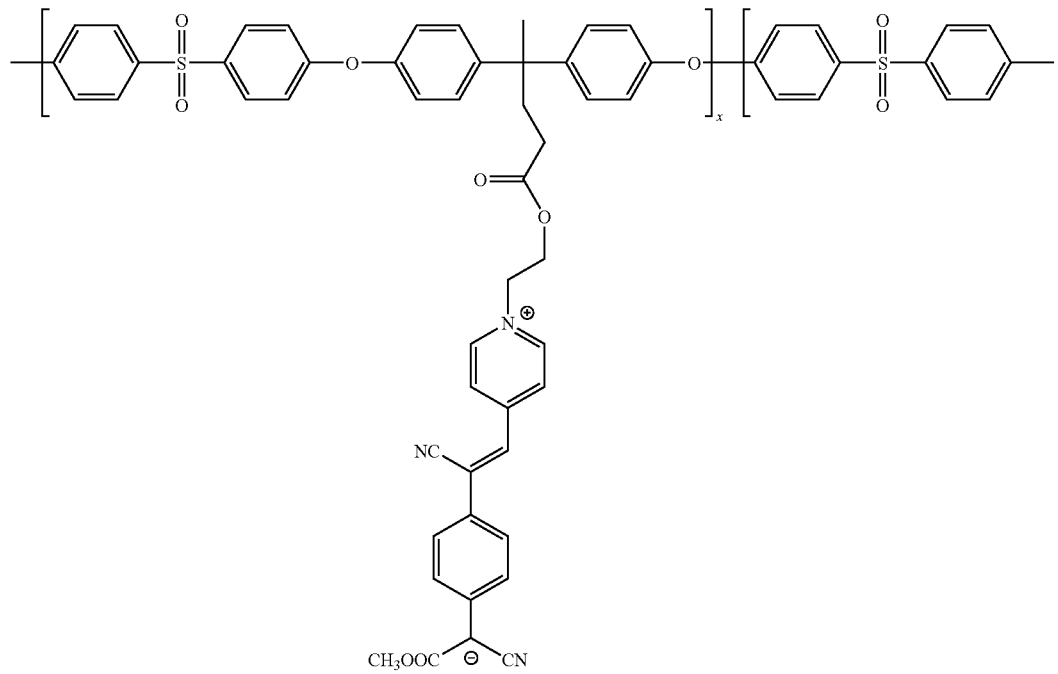

IV-a

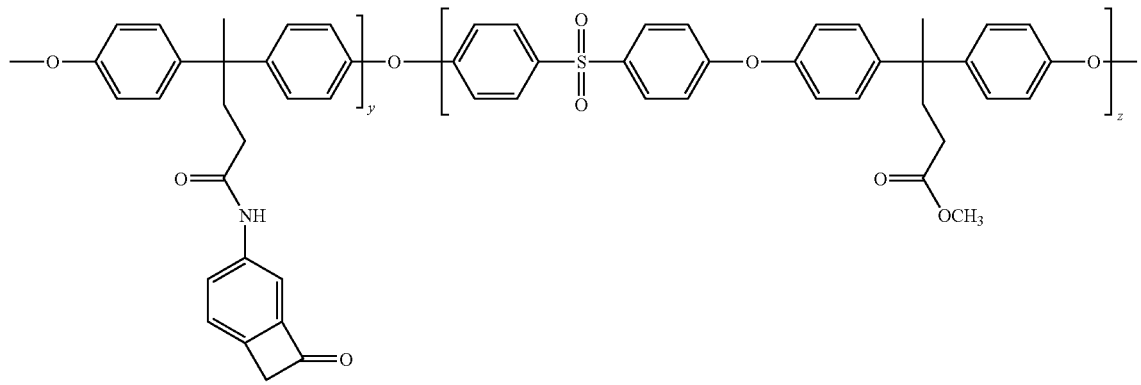

Polymerization of dihydroxy-containing chromophores III and III', such as IIIb derived from Id and IIa, with diacid chloride in the presence or absence of a comonomer such as bisphenol A, ethylene glycol or polyol, afford the corresponding (co)polyesters with the chromophore content in the range of 5% to 50% by molar ratios relative to the other comonomers used. The acid chlorides can be selected from the commercial sources, such as terephthaloyl chloride, isophthaloyl chloride and adipoyl chloride. Thus, polymerization is typically done in dry DMF or DMAC, in the presence of pyridine or triethylamine, using an equimolar amount of IIIb and adipoyl chloride at temperatures ranging from 25° C. to 150° C. The resulting polymer IV-b is isolated as blue powders and can be dissolved in common organic solvents for casting the films on ITO glass.

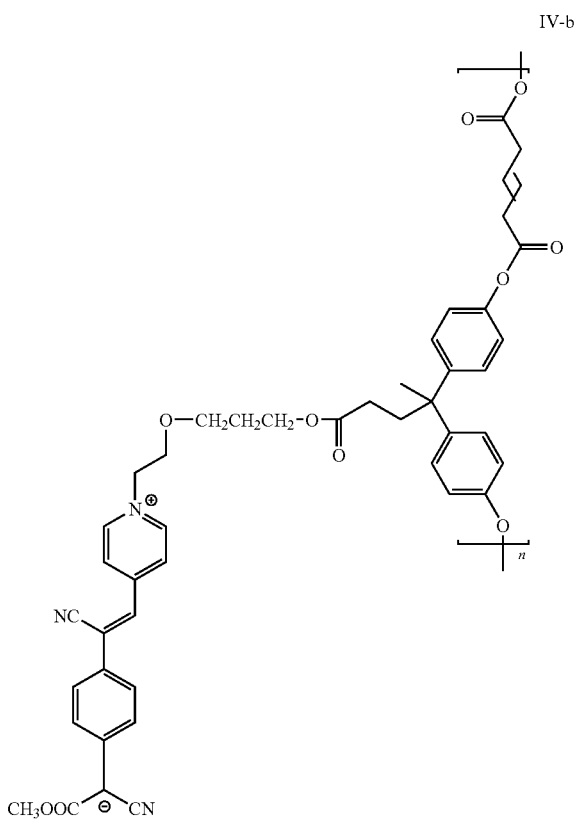

IV-b

A polymer is formulated by mixing a certain amount, typically 1% to 30% by weight relative to a host polymer, and in some embodiments of the invention, 5-15% by weight, of a chromophore III or III' in a host polymer such as poly(methyl methacrylate), polycarbonate, poly(vinyl pyrrolidinone), polysulfone and polyimide in organic solvent.

The polymer films in a thickness of 0.5-5.0 micron, preferably 1.5-3.0 micron, suitable for poling and testing of EO coefficients are prepared by casting or spin coating a formulated polymer solution on ITO glass plates and dried in oven at elevated temperatures. A thick layer of gold electrode is then sputtered onto the surface of the dried film. During the contact poling, the electric field is turned on at 100° C. and the voltages applied across the films are maintained in a range of 0.6-0.8 MV/cm while keeping the current across the films below 10 μA. The standard Teng-Man ellipsometric setup is used to measure the EO coefficient ($r_{33}$ at 1550 nm) of the poled samples.

EXAMPLES

The invention will be further described with reference to the following examples, which are intended to be illustrative of the invention but not limitative.

A—Preparation of Picolinium Salts (Formula I)

Example 1

N-(2-hydroxyethyl)-4-picolinium bromide (Ia) and its Derivative Ie

In a 3-neck, round-bottomed flask flushed with nitrogen, 2-bromo-1-ethanol (40.01 mmol), 4-picoline (43.57 mmol) and absolute ethanol (16 mL) were combined and heated for 3.5 hours at 50° C. under nitrogen with stirring. The reaction was stopped and the contents of the flask were transferred to a one-neck round-bottomed flask. The solvent was removed under vacuum and the residue was washed with diethyl ether (4×100 mL) and any remaining solvent was removed under vacuum. The product was obtained as a viscous orange liquid in 34% yield. $^1$H NMR (200 MHz, CDCl$_3$) 8.9 (2H, protons on pyridine ring), 8.0 (2H, protons on pyridine ring), 2.6 (3H, CH$_3$), 4.6 (2H, —CH$_2$O), 3.8 (2H, —NCH$_2$—), 5.2 (1H, —OH); IR (neat, cm$^{-1}$) 3303 (OH), 1640 (aromatic C=N), 1474 (aromatic C=C).

The esterification reaction of Ia with the corresponding acid chloride or anhydride (which is derived from 4,4-bis(4-hydroxyphenyl)valeric acid) was carried out in chloroform in the presence of 2 moleq. of dry pyridine at room temperature. The product Ie was isolated by first removing chloroform and washing with diluted HCl solution. It was characterized by IR, which showed the peak at 1730 cm$^{-1}$ for the ester group and disappearance of the OH peak at 3300 cm$^{-1}$.

Example 2

N-Hexyl-4-picolinium bromide (Ib)

A solution of 4.65 g of 4-picoline (50 mmol), 9.90 g of 1-bromohexane (60 mmol) and 30 mL of acetonitrile was refluxed for three hours and then cooled to room temperature. The viscous mixture was then added dropwise into 100 mL of ether with vigorous stirring. The mixture was let to stand for a while and then the upper ether layer was decanted. The residual viscous solution was dissolved in 10 mL of acetonitrile again and dispersed into 100 mL of ether. This procedure was repeated two more times in order to completely remove the unreacted starting materials. The resulting viscous liquid was dried under vacuum to give 11.8 g of off-white wax (92% yield). $^1$H NMR (DMSO-d$_6$, 400 MHz): 0.89 (t, 3H), 1.26 (m, 4H), 1.85 (m, 4H), 2.64 (s, 3H), 4.81 (t, 2H), 8.0 (m, 2H), 8.9 (m, 2H); IR (CHCl$_3$, cm$^{-1}$): 1398 (C=C), 1635 (C=N), 2975 (N—C).

Example 3

N-Benzyl-4-methylpyridinium chloride (Ic)

A solution of 2.53 g of benzyl chloride (20 mmol), 1.86 g of 4-picoline (20 mmol) and 20 mL of acetonitrile was refluxed for three hours, cooled to room temperature and then frozen in refrigerator. Pale pink crystals precipitated from the solution, which were collected by filtration and washed with ether (3×5 mL) to afford 4.09 g of the product (92% yield). $^1$HNMR (DMSO-d$_6$, 400 MHz): δ 9.1 (s, 2H), 8.0 (d, 2H, J=6.24), 7.5 (s, 2H), 7.4 (m, 3H), 5.8 (s, 2H), 2.6 (s, 3h); $^{13}$C NMR (DMSO-d$_6$, 100 MHz): δ 159.0, 143.5, 134.3, 128.9, 128.8, 128.3, 61.9, 21.1.

Example 4

Picolium bromide Id

To a solution of 4,4-bis(4-hydroxyphenyl)valeric acid (2.86 g, 10.0 mmol) in DMF (30 mL) was added KHCO$_3$ (1.25 g, 12.5 mmol). After stirring for 30 min at 80° C., 1,3-dibromopropane (6.05 g, 30.0 mmol) was added dropwise. The reaction mixture was stirred at 80° C. for another 5 h before being cooled to room temperature and then poured into distilled water (250 mL). Ethyl acetate (3×50 mL) was used to extract the product. The extracts were combined, washed with saturated NaCl solution, dried over anhydrous magnesium sulfate. After removal of the solvents, the intermediate bromide was purified by column chromatography (silica gel, hexane/ethyl acetate: 1/1 v/v) and obtained as a syrup: 2.65 g (65% yield); $^1$H NMR (200 MHz, CDCl$_3$): 8.03 (s, 2H), 7.02-6.71 (dd, 8H), 4.16 (t, 2H), 3.40 (t, 2H), 1.95 (p, 2H), 1.54 (s, 3H), 1.26 (t, 2H). A solution of the intermediate bromide (2.65 g, 6.50 mmol) and 4-picoline (0.67 g, 7.20 mmol) in acetonitrile (50 mL) was heated to reflux under nitrogen for 5 h. After cooling to room temperature, the reaction mixture was poured into diethyl ether (200 mL). The white precipitate was collected by filtration, washed with diethyl ether (2×10 mL) and vacuum dried at 40° C. to give the corresponding picolinium salt Id: 1.30 g (40% yield); $^1$H NMR (200 MHz, DMSO-d$_6$): 9.20 (s, 2H), 8.94-7.96 (dd, 4H), 6.91-6.64 (dd, 8H), 4.60 (t, 2H), 4.05 (t, 2H), 2.56 (s, 3H), 2.2 (m, 2H), 1.45 (s, 3H), 1.09 (t, 2H).

Example 5

N-Hexyl-2,4-dimethylpyridinium bromide (Ih)

1-Bromohexane (1 equivalent) was dissolved in some toluene in a round bottomed flask flushed with nitrogen. Then, lutidine (1 equivalent) was added and the mixture was heated to reflux. During the reaction, a brown product appeared. The reaction was stopped after 8 hours. Afterwards, the solvent was removed under the reduced pressure. A minimum amount of acetonitrile was added to dissolve the residue and ether was added to precipitate the product. The crude product was washed with ether to afford off-white crystals. The yield of the reaction is 83%. $^1$H NMR (CDCl$_3$, 200 MHz): δ 0.89 (t, 3H), 1.26 (m), 1.85 (m), 2.64 (s, 3H), 2.93 (s, 3H), 4.81 (t, 2H), 7.75(d, 2H), 9.51 (d, 1H); IR (CHCl$_3$, cm$^{-1}$): 1398 (C=C), 1635 (C=N), 2975 (N—C).

Example 6

N-(3-hydroxypropanyl)-2,4-dimethylpyridinium bromide (Ii)

3-Bromopropanol (3,5 equivalents) was dissolved in some toluene in a round-bottomed flask flushed with nitrogen. Then, lutidine (1 equivalent) was added and the mixture was heated to reflux. After several hours, an off-white product appeared in the flask as a sticking solid. The reaction was stopped after 18 hours. The solvent was removed under the reduced pressure and ether was added to precipitate out the solids. After washing with ether, the product as off-white powders were dried. The yield of the reaction is 83%. The product is soluble in acetone, methanol and acetonitrile but not in diethyl ether. $^1$H NMR (CDCl$_3$, 200 MHz): δ 2.24 (m, 2H), 2.61 (s, 3H), 3.03(s, 3H), 3.70 (t, 2H, J=4.86), 5.14 (t, 2H, J=7.26), 7.67 (s, 1H), 7.81(d, 1H, J=6.06), 9.65 (d, 1H, J=6.52); IR (CHCl$_3$, cm$^{-1}$): 1642 (C=C) (C=N), 3432 (O—H).

Example 7

Substituted picolinium salt (Ij)

4,4'-Dimethyl-2,2'-bipyridine (0.5247 g, 0.0028 mol) was dissolved in an excess of 5 mL of methyl iodide in a 1-neck 100 mL round-bottomed flask equipped with a magnetic stirrer. The solution was refluxed at 40° C. for 24 hours. In addition, the entire reaction vessel was kept in darkness to prevent the reaction from photo reacting. The reaction was halted after 24 hours and the excess methyl iodide was removed by rotary evaporation. Upon the removal of the methyl iodide, white crystals were collected in 91% yield (0.80 g) with a melting point of 169-176° C. $^1$H NMR (DMSO-d$_6$, 400 MHz): δ 2.47 (s, 3H), 2.65 (s, 3H), 4.19 (s, 3H), 7.55 (d, 1H), 7.79 (s, 1H), 8.06 (d, 1H), 8.13 (s,1H), 8.70(d, 1H), 9.01 (d, 1H); MS (SI, H$_2$O, m/e) 199.1 (M$^+$); IR (KBr, cm$^{-1}$): 3430 (C—N), 3020 (C—H), 1601, 1212 (C=C).

Example 8

Substituted picolinium bromide (Ik)

4,4'-Dimethyl-2,2'-bipyridine (0.100 g, 0.0005 mol) was combined with 2 molar equivalents of 3-bromopropanol (0.151 g, 0.0011 mol) and 5 mL of absolute ethanol in a one necked 100 mL round-bottomed flask equipped with a magnetic stirrer. The solution was refluxed at 80° C. for 24 hours. Later, a white precipitate was achieved following the addition of 20 mL of ether. The white precipitate was then filtered from the solution. The white product was air dried with the aid of a vacuum for 3 hours. The final product was a white powder with a 73% yield (0.1831 g) and a melting point of 169-176° C. $^1$H NMR (DMSO-d$_6$, 200 MHz): δ 2.6 (s, 3H), 2.8 (s, 3H), 3.9 (m, 1H), 5.25 (s, 2H), 7.7 (d, 1H), 8.3 (d, 2H), 8.55 (s, 1H), 8.75 (s, 1H), 9.1 (s, 1H), 9.2 (d, 1H).

B—Preparation of Compounds II

Example 9

7,8-Bis(methoxycarbonyl)-7,8-dicyanoquinodimethine (IIa)

The product was synthesized, starting from 1,4-phenylenediacetonitrile which was first converted to 7,8-bis(methoxycarbonyl)-7,8-dicyano-p-xylene using dimethylcarbonate, followed by oxidation with bromine, according to the reported method (Iwatsuki, S.; Itoh, T.; Iwai, T.; Sawada, H. *Macromolecules* 1985, 18, 2726. ). The product was isolated as yellow solids. IR (KBr, cm$^{-1}$): 2208 ($v_{C\equiv N}$), 1728 and 1716 ($v_{c=o}$). $^1$HNMR (CDCl$_3$, 200 MHz): 8.4-8.5 (m, 2H), 7.4-7.5 (m, 2H), 4.78 (s, 2H), 3.96 (s, 6H); MS (EI, m/e): 270 (M$^{+\bullet}$).

Example 10

7,8-Bis(2-hydroxyethoxycarbonyl)-7,8-dicyanoquinodimethine (IIb) and Its Derivatives IId and IIe This compound was synthesized in the similar way as in Example 9, except that ethylene carbonate is used in the first-step reaction instead of dimethylcarbonate. IR (Neat, cm$^{-1}$): 3400 ($v_{O-H}$), 2210 ($v_{C\equiv N}$), 1716 ($v_{c=o}$); MS (EI, m/e): 330 (M$^{+\bullet}$).

The compound IId was easily prepared by reacting the precursor of IIb with α-chloroacetyl chloride in chloroform in the presence of 2 equivalents of pyridine at room temperature over night, followed by treatment of sodium azide (3 equivalents) at room temperature for 6-18 hours. The product is isolated and further oxidized as described in Example 9 according to the known procedure. IR (Neat, cm$^{-1}$): 2115 ($v_{N3}$), 1716 ($v_{c=o}$); MS (EI, m/e): 496 (M$^{+\bullet}$).

Similarly, compound IIe was obtained by reacting the precursor of IIb with the known acid chloride shown below in chloroform in the presence of 2 equivalents of pyridine at room temperature over night. The intermediate was further oxidized with bromine as described in Example 9. IR (Neat, cm$^{-1}$): 1728 (ester $v_{c=o}$), 1716 ($v_{c=o}$); Electrospray MS: 2282 (M=H$^+$).

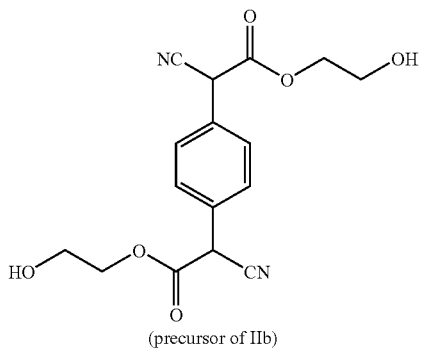

(precursor of IIb)

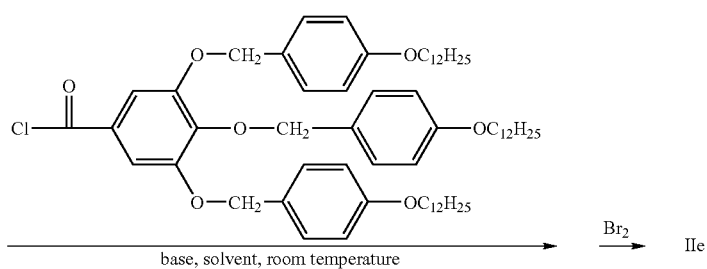

Example 11

7,8-Bis(propargyl)-7,8-dicyanoquinodimethine (IIc)

This compound was synthesized in the similar way as in Example 9, except that bis(propargyl)carbonate is used in the first-step reaction instead of dimethylcarbonate. IR (Neat, cm$^{-1}$): 2132 ($v_{C\equiv C}$), 2210 ($v_{C\equiv N}$), 1716 ($v_{c=o}$); MS (EI, m/e): 318 (M$^{+\bullet}$).

Example 12

Compound IIf (R=CH$_3$)

This compound was synthesized, starting from a known compound, 2,5-dibromo-α,α-dicyano-p-xylene, as shown below. According to the known procedure by Lebedev, S. A., et al (*J. Organomet. Chem.* 1998, 344, 253), the Ni-catalyzed coupling reaction with methyl acrylate proceeded as expected to form the corresponding intermediate, which was isolated and could be purified by chromatography or used directly without further purification. The subsequent two reactions, namely the reaction with dimethylcarbonate and the oxidation with bromine, were followed the procedures as described in Example 9 and the reference cited therein. The overall yield in three steps was in a range of 10-30%. IR (KBr, cm$^{-1}$): 2208 ($v_{C\equiv N}$), 1728 and 1716 ($v_{c=o}$). $^1$H NMR (CDCl$_3$, 200 MHz): 7.5 (s, 2H), 4.78 (s, 2H), 3.96 (s, 6H), 3.83 (s, 6H), 2.2 and 3.2 (dd, 8H, —CH$_2$CH$_2$—); MS (EI, m/e): 442 (M$^{+\bullet}$). The product IIf could be used without further purification for making the desired chromophores III and III'.

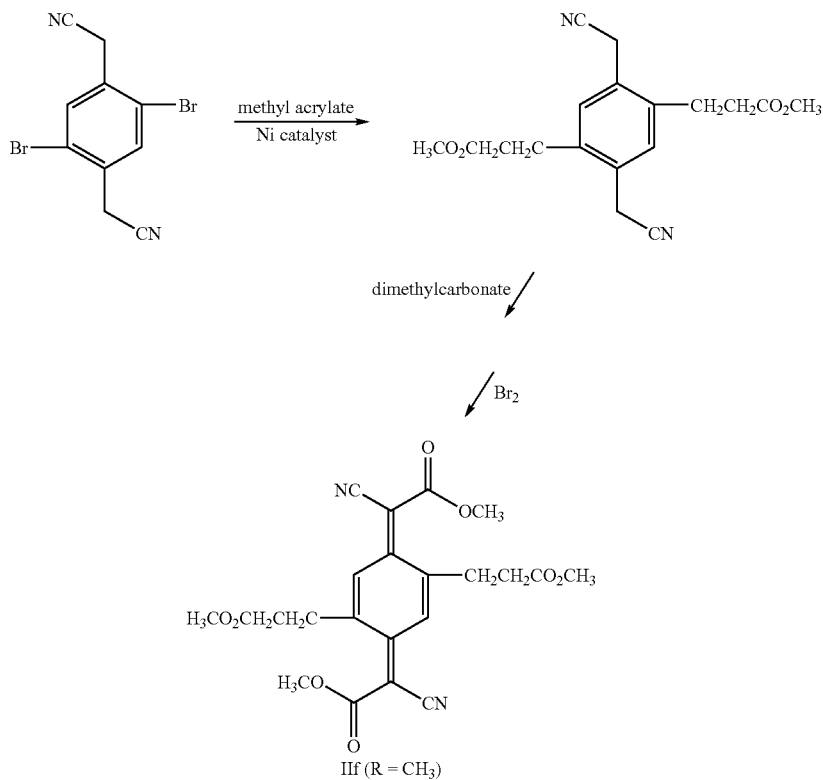

Example 13

Synthesis of II-m

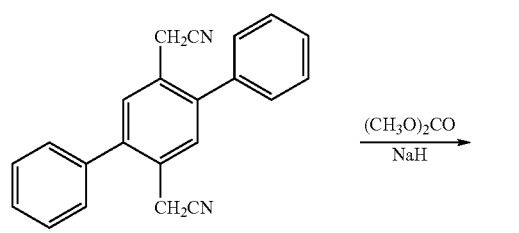

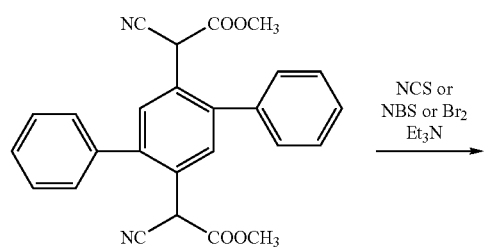

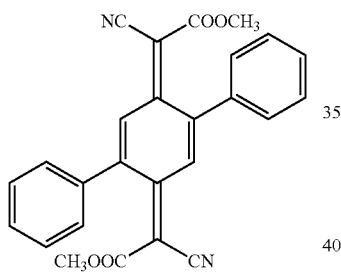

Sodium hydride (0.09 g, 60% in oil, 2.24 mmol) was added to 0.15 g of the starting dicyano compound in 5 mL of dimethyl carbonate under nitrogen. The resulting mixture was stirred at room temperature for 2 days. The reaction mixture was placed under reduced pressure to remove the solvent. To the residue obtained was added sufficient hydrochloride acid to bring the pH of the mixture to about 1-3, and an additional 20 mL of water was then added. The mixture was extracted with 40 mL of ethyl acetate twice. The extracts were washed well with water, dried over anhydrous sodium sulfate, and evaporated under reduced pressure to remove ethyl acetate. The residue was recrystallized from methanol and was then dissolved in 20 mL of acetonitrile under nitrogen. At 0° C., N-chlorosuccinimide or N-bromosuccimide (4 mmol) was added to the solution followed by addition of 2 mmol of triethylamine. Yellow precipitates were collected by filtration with or without concentration of the solvent to give the final compound II-m that could be further purified by recrystallization.

C—Preparation of Zwitterionic Chromophores (formula III and III')

A series of chromophores III and III' were synthesized by the new reaction of picolinium halides I and compounds II in the presence of a base and at least one organic solvent. The generality and applicability for the syntheses of all the chromophores as shown in, but not limiting to, formula III and III', are demonstrated by the following examples. Preferably, the reaction is carried out at reflux temperature and followed by UV-Vis.

The base is an amine or nitrogen heterocyclic. The preferred bases are pyridine, quinoline, 1,8-diazabicyclo[5,4,0]undec-7-ene (DBU), 1,4-diazabicyclo[2,2,2]octane (DABCO), N-methyl piperidine, and N-(2-hydroxyethyl)piperidine. Particularly preferred bases are DBU, DABCO and N-(2-hydroxyethyl)piperdine. It was noted that the choice of solvent and base had an effect on the purity and yield of the chromophore product. The solvents such as methanol, ethanol or acetonitrile) are preferred, although other organic solvents can be used if they give acceptable purity and yield. Similarly, the best purity and yield were found to occur with the particularly preferred bases, but other bases can be used.

Example 14

Chromophore IIIa (derived from Ib and IIa)

To a refluxed suspension of 0.5000 g (1.85 mmol) 7,8-bis(methoxycarbonyl)-7,8-dicyanoquinodimethane, 0.2387 g (0.925 mmol) of N-hexyl-4-methylpyridinium bromide and 25 mL of anhydrous methanol, a solution of 0.2812 g of DBU (1.85 mmol) in 5 mL of methanol was added dropwise in portions of 1 mL every 30 minutes. The reaction was monitored by UV-vis of the sample made by diluting a small amount of reaction mixture in DMF. The reaction was stopped until the characteristic peaks of radical anion almost disappeared and chromophore peak became the major intense peak. Generally, the reaction needs to reflux for 4-5 hours after completion of adding the DBU solution. The reaction mixture was then cooled to 0° C. with ice bath and the product was filtered. The obtained deep blue solid was washed with anhydrous methanol (3×5mL) and anhydrous ether three times (3×5 mL) respectively. Pure product was obtained in 0.17 g (48% yield). $^1$H NMR (DMSO-$d_6$, 400 MHz): 8.9 (d, 2H), 8.3 (d,2H), 7.8 (s, 1H), 7.6(b, 2H), 7.5 (d, 2H), 4.5 (t, 2H), 3.4 (s, 3H), 1.9 (m, 2H), 1.2 (s, 6H), 0.8 (t, 3H); $^{13}$C NMR (DMSO-$d_6$, 100 MHz): 167.4, 149.5, 147.1, 144.1, 126.7, 125.2, 125.0, 121.1, 120.7, 119.8, 116.9, 59.9, 49.1, 30.5, 30.3, 25.0, 21.8, 13.8; MS (ESI, m/e): 388 (M+H$^+$); IR (KBr, cm$^{-1}$): 2227 and 2155 ($v_{C \equiv N}$), 1752 ($v_{C=O}$).

Example 15

Chromophore IIIb (derived from Id and IIa)

The same procedure as described in Example 14: 0.46 g (0.925 mmol) of 1d was used and 0.28 g of IIIb was obtained, in 48% yield. $^1$H NMR (DMSO-$d_6$, 400 MHz): 9.1 (s, 2H), 8.9 (d,2H), 8.3 (d,2H), 7.8 (s, 1H), 7.7(b, 2H), 7.6 (d, 2H), 6.9(d, 4H), 6.6 (d, 4H), 4.5 (t, 2H), 4.1 (t, 2H), 3.5 (s, 3H), 2.2 (m, 4H), 1.9 (t, 2H), 1.4 (s, 3H). $^{13}$C NMR (DMSO-$d_6$, 100 MHz): 172.7, 167.3, 154.9, 149.5, 147.1, 144.3, 138.9, 127.6, 127.1, 126.6, 124.8, 124.7, 121.0, 120.7, 119.8, 116.7, 115.7, 114.7, 114.5, 60.9, 57.5, 49.0, 43.5, 35.9, 32.9, 29.5, 29.1, 27.0; IR (KBr, cm$^{-1}$): 3401 ($v_{O-H}$), 2226 and 2155 ($v_{C\equiv N}$), 1733($v_{c=o}$); MS (ESI, m/e): 630 (M+H$^+$).

Example 16

Chromophore IIIc (derived from Ia and IIa)

The procedure of Example 14 was followed, using 0.20 g (0.925 mmol) of picolinium salt Ia and 0.14 g of IIIc as blue solids was obtained (44% yield). $^1$H NMR (DMSO-$d_6$, 400MHz): 8.8 (d, 2H), 8.3 (d, 2H), 7.8 (s, 1H), 7.6 (b, 2H), 7.5 (d, 2H), 5.2(t, 1H), 4.5 (t, 2H), 3.8 (q, 2H), 3.4 (s, 3H); $^{13}$C NMR (DMSO-$d_6$, 100 MHz): 167.3, 149.5, 147.0, 144.5, 126.6, 125.2, 124.9, 124.6, 121.0, 120.6, 119.7, 116.8, 62.2, 59.9, 49.0; IR (KBr, cm$^{-1}$): 3332 ($v_{O-H}$), 2226 and 2161 ($v_{C\equiv N}$), 1751($v_{c=o}$); MS (ESI, m/e): 348 (M+H$^+$).

Example 17

Chromophore IIId (derived form Ic and IIa)

The procedure of Example 14 was followed, using 0.20 g of N-benzyl-4-methylpyridinium chloride (Ic) and 0.17 g of the product was obtained (47% yield). $^1$H NMR (DMSO-$d_6$, 400 MHz): 9.0 (d, 2H), 8.3 (d, 2H), 7.8 (s, 1H), 7.6 (b, 1H), 7.4-7.5 (m, 7H), 5.7 (s, 2H), 3.5 (s, 3H); $^{13}$C NMR (DMSO-$d_6$, 100 MHz,): δ 167.3, 149.8, 147.2, 144.0, 134.3, 129.2, 129.1, 128.6, 126.7, 125.1, 124.8, 121.1, 120.7, 119.9, 116.7, 62.3, 61.1, 49.0; IR (KBr, cm$^{-1}$): 2226 and 2146 ($v_{C\equiv N}$), 1750 ($v_{c=o}$). MS (ESI, m/e): 394 (M+H$^+$).

Example 18

Chromophore IIIe (derived form Ic and IIb)

The procedure of Example 14 was followed except that the reaction was heated to reflux, using 0.20 g of N-benzyl-4-methylpyridinium chloride (Ic) and the product was obtained in 22% yield. The $^1$H NMR spectrum of the product resembles closely to that of IIIc, except for the difference due to the hydroxyethyl moiety.

Example 19

Chromophores III-f and III-g

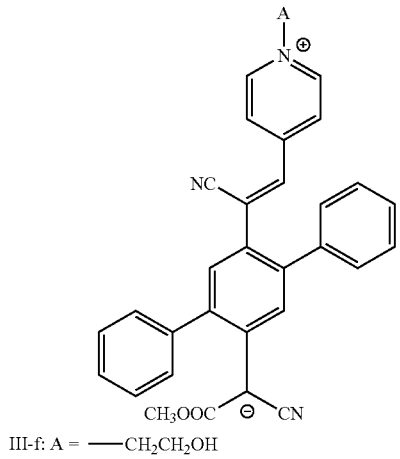

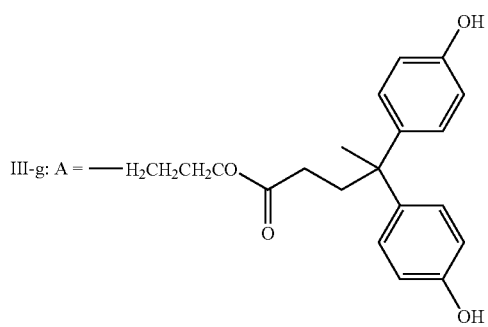

These chromophores were prepared in the same way as described in Example 14, using Ia and Id, respectively.

III-f: 55% yield. $^1$H NMR (DMSO-$d_6$, 400MHz): 8.9 (d, 2H), 8.3 (d, 2H), 7.8 (s, 1H), 7.4-7.6 (m, 12H), 5.2 (t, 1H), 4.5 (t, 2H), 3.8 (q, 2H), 3.4 (s, 3H); IR (KBr, cm$^{-1}$): 3332 ($v_{O-H}$), 2226 and 2161 ($v_{C\equiv N}$), 1751($v_{c=o}$); MS (ESI, m/e): 500 (M+H$^+$).

III-g: 45% yield. $^1$H NMR (DMSO-$d_6$, 400MHz): 9.0 (s, 2H), 8.9 (d, 2H), 8.3 (d, 2H), 7.8 (s, 1H), 7.4-7.7 (m, 12H), 6.9 (d, 4H), 6.6 (d, 4H), 4.5 (t, 2H), 4.1 (t, 2H), 3.5 (s, 3H), 2.2 (m, 4H), 1.9 (t, 2H), 1.4 (s, 3H); IR (KBr, cm$^{-1}$): 3401 ($v_{O-H}$), 2226 and 2155 ($v_{C\equiv N}$), 1733($v_{c=o}$); MS (ESI, m/e): 783 (M+H$^+$).

Example 20

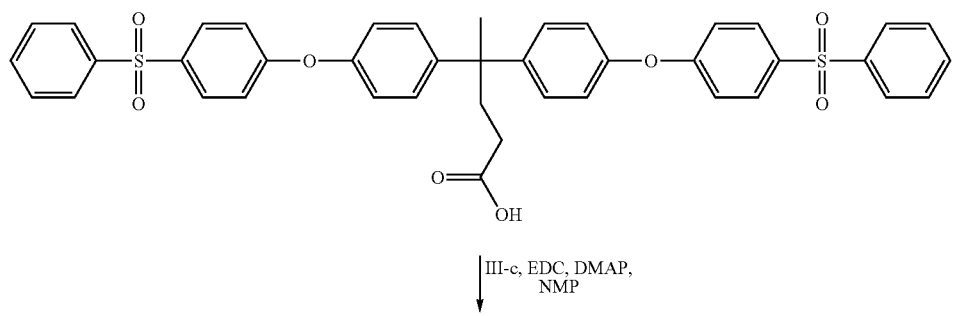

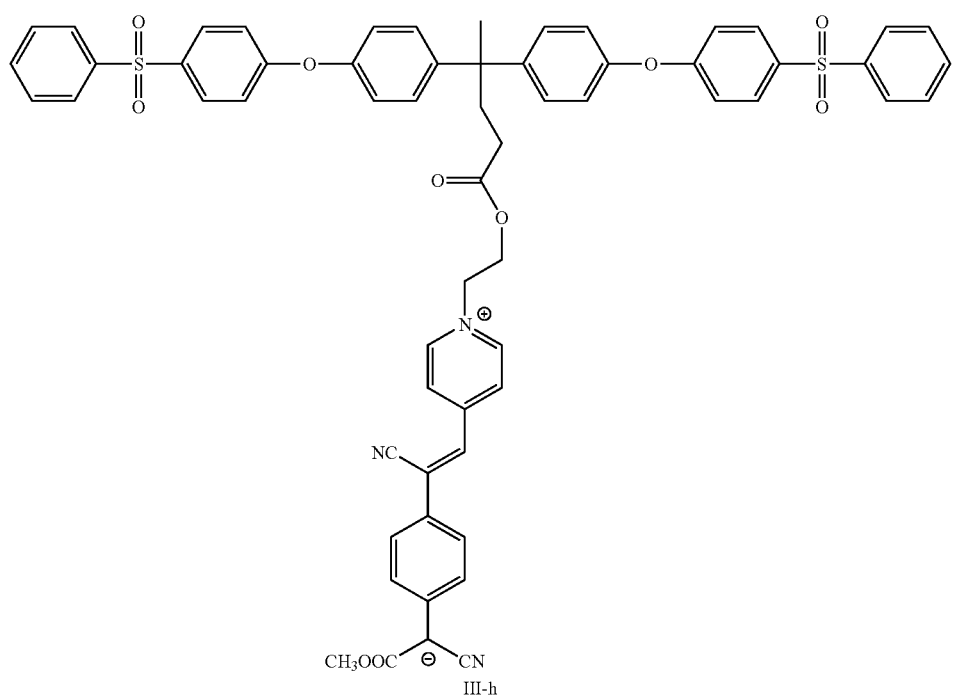

A mixture of 4-chlorophenyl sulfone (2.2 moleq) and 4,4'-bis(4-hydroxyphenyl)valeric acid (1.0 moleq) in the presence of 2.5 moleq of $K_2CO_3$ in DMAc (20% wt/V) was heated to reflux under nitrogen for 18 hours. The product was isolated by pouring the reaction mixture into water. After drying in oven at 80° C., it was mixed with chromophore III-c (1.0 moleq) in dry NMP, followed by addition of EDC (1.65 moleq) and DMAP (1.5 moleq). After stirring at room temperature under argon for 1 day, the reaction mixture was poured into water. The product III-h was collected by filtration and passed through a short column (silica gel, washing with THF). This chromophore shows a Tg of 120° C. by DCS and a maximum absorption at 683 nm (in DMF).

D. Incorporation of Zwitterionic Chromophores into Host Polymer

Example 21
Grafting III-c onto an acid-containing host polymer
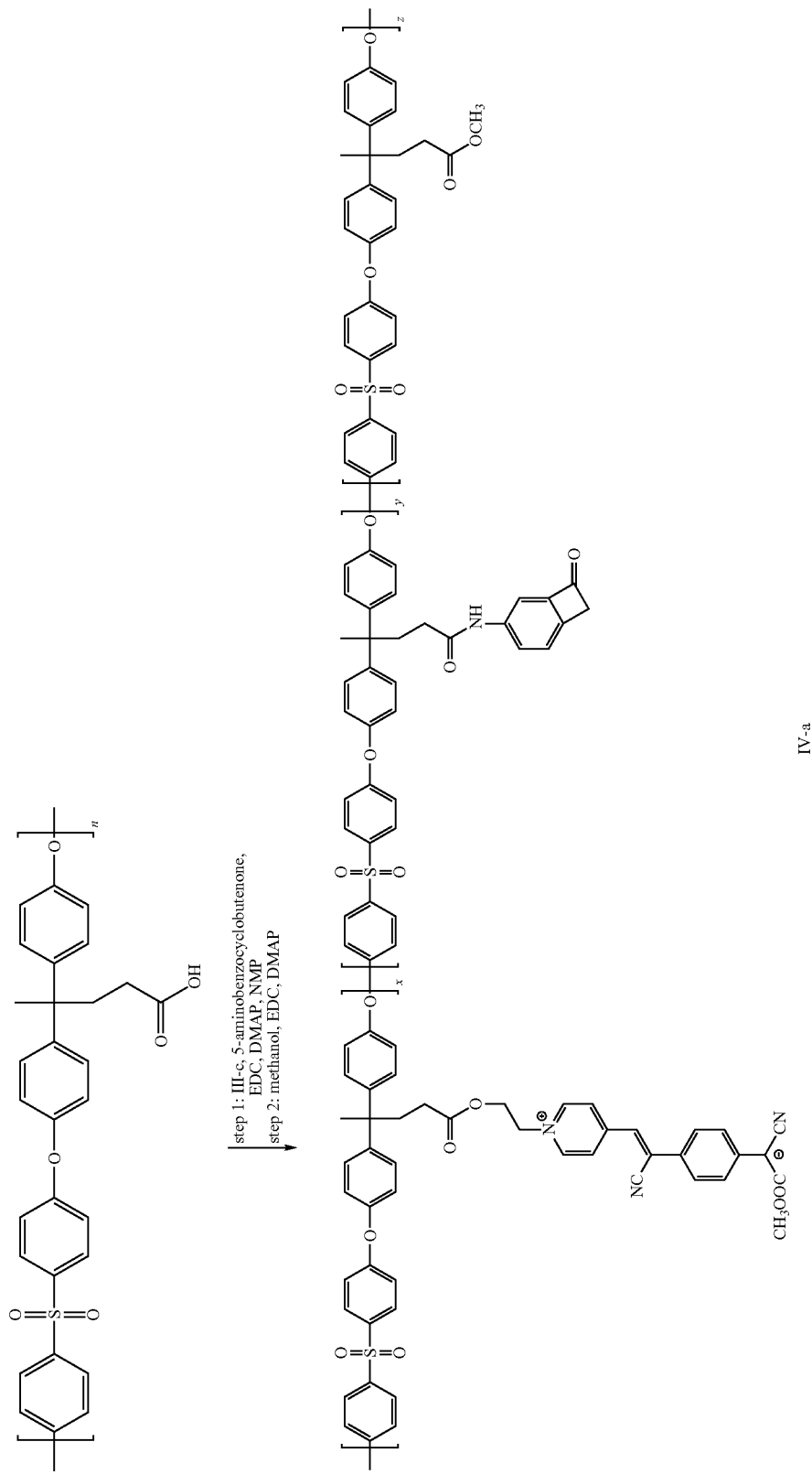
IV-a

The acid-containing poly(ether sulfone) was prepared according to a known procedure and used a host polymer, as an example, for grafting the hydroxy-containing zwitterionic chromophores III and III'. The amounts of chromophore III-c and 5-aminobenzocyclobutenone were 15 mole % and 5 mole %, respectively, relative to the host polymer. The amount of DMAP and EDC were 1.65 eq and 1:5 eq respectively. The mixture of 250 mg (0.5 mmol) of acid-containing poly(ether sulfone), 27 mg of chromophore III-c, 15mg of DMAP, 21 mg of EDC and 5 mL of anhydrous NMP was stirred at room temperature under argon for 1 day. Then, 7 mg of 5-aminobenzocyclobutenone, 5 mg of DMAP and 7 mg of EDC were added to the reaction solution and the reaction continued for another day. Finally, 0.08 mL of methanol, 80 mg of DMAP and 112 mg of EDC were added to the reaction solution and the reaction continued for 2 more days. The final reaction solution was added dropwise into 100 mL of methanol to precipitate the polymer product. Then the polymer was dried in vacuum at 50° C. overnight and 0.27 g of polymer IV-a was obtained. The chromophore content was determined by UV-Vis calibration method and found to be 4.82% by weight relative to the whole polymer or 9% by molar ratio in the whole polymer. Its decomposition temperature ($T_d$) is 293° C. (5% weight loss) by TG analysis, its $T_g$ is 155° C. and its onset temperature for crosslinking is at 180° C. After heat curing, the polymer had a $T_g$ of 175° C. by DSC.

The obtained chromophore-containing polymers showed good solubility in polar aprotic solvents such as tetrahydrofuran (THF), DMAC), DMAc, and DMSO. The polymer solution in DMAc can be used to cast films. The cast thin films are transparently blue, flexible, tough, and can be peeled off from substrate as a free-standing film. Upon thermal treatment, these polymers were insoluble in common organic solvents tested, due to the crosslinking of the benzocyclobutenone moiety within the polymers.

Example 22

Preparation of Linear Polyester from IIIb

An equimolar amount of IIIb and adipoyl chloride were dissolved in dry DMF (in a total of 20% g/mL). To this solution, dry pyridine (2.5 moleq.) was added slowly via a syringe at room temperature while a stream of nitrogen was passing through the reaction flask. After completion of addition, the reaction mixture was stirred at 80° C. overnight. After precipitation into methanol, the blue polymer IV-b was isolated in about 70% yield. This polymer can be dissolved in common organic solvents for casting the films on ITO glass. Its decomposition temperature ($T_d$) is above 250° C. (5% weight loss) by TG analysis and its $T_g$ is around 125° C.

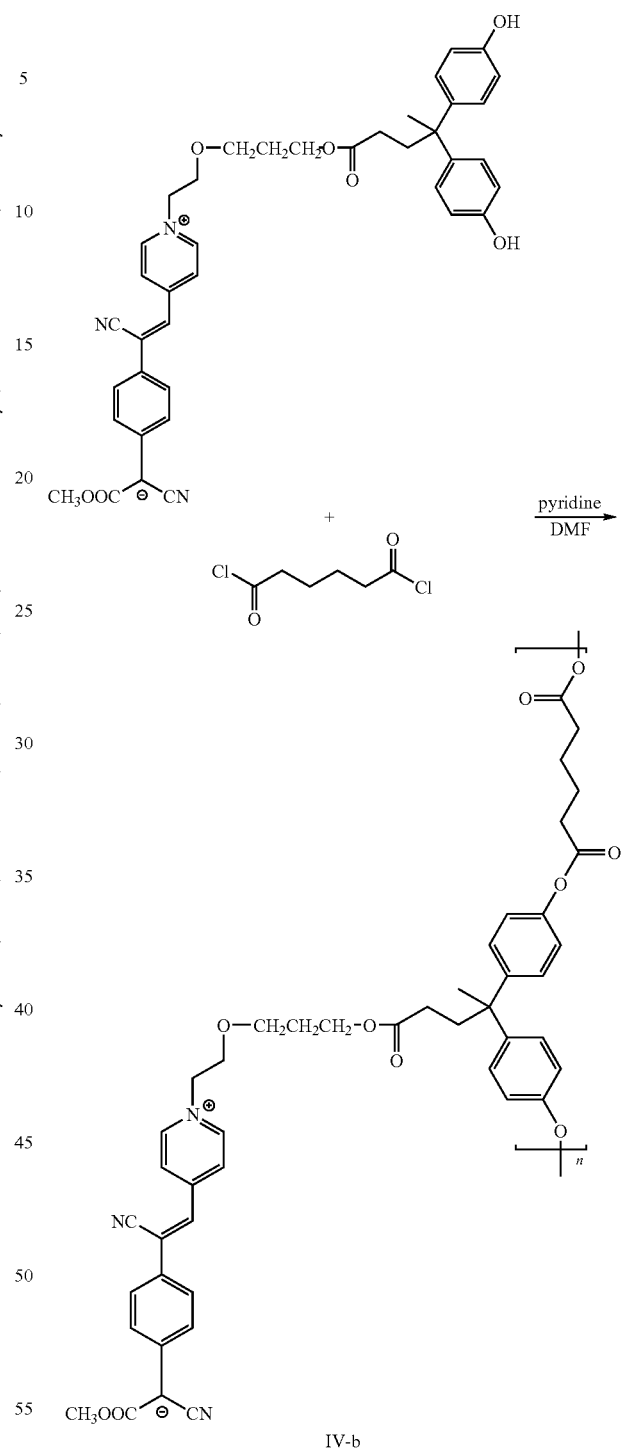

E—Preparation of Chromophore-Doped Polymers, Poled Films and Testing of EO Coefficients Example 23

A mixture of chromophore IIId (5% by weight) and polysulfone (Ultrason™ E3010, $T_g$=227° C., 95% by weight) were dissolved in DMF (solution concentration: 10-15% by weight). The film was cast on ITO glass and dried in oven at temperatures up to 150° C. The dried film had a Tg of 205° C., which helps to set the poling temperature range. The film thickness can be controlled by the amount of the polymer solution applied on the ITO glass and also the concentration of the said solution. The film on ITO glass was then coated with a thin layer of gold by sputtering.

The poling conditions were selected to be 70 V/μm of the applied voltages across the film, heating at 190° C., under nitrogen and poling or holding time ranging from 1 minute to 60 minutes. Two film samples with a different thickness were tested for the EO coefficients (in the table below). Both of them gave an exceptionally large $r_{33}$ values at 1550-nm communication wavelength, which are about twice larger than that of $LiNbO_3$ currently being used in EO modulator. The stability of the poled NLO films was tested. The EO coefficient was monitored while the sample films were kept at 80° C. over a period of 1500 hours. It was found that there no change in $r_{33}$ values within the testing period. Such an NLO polymer film can be used in electro-optic modulators.

|  | Poling Voltage (V/μm) | Poling Temperature (° C.) | Poling Time (minutes) | E-O coefficient ($r_{33}$, pm/V, at 1550 nm) |
| --- | --- | --- | --- | --- |
| Film 1 (1.6 μm) | 70 | 190 | 1 | 56 |
| Film 2 (1.8 μm) | 70 | 190 | 1 | 61 |

Example 24

It is the same as in Example 28, except that the film of 8% by weight of IIId in polysulfone was prepared. The Tg of the film is 197° C. The thickness of films is in a range of 1.3-2.4 micron. After poling, the $r_{33}$ value of 49 pm/V at 1550 nm was obtained for a film sample with a thickness of 1.7 micron. Such an NLO polymer film can be used in electro-optic modulators.

Example 25

It is the same as in Example 28, except that the film of 10% by weight of IIId in polysulfone was prepared. The Tg of the film is 211° C. The thickness of films is in a range of 1.0-2.0 micron. After poling, the $r_{33}$ value of 22 pm/V at 1550 nm for a film with a thickness of 1.2 micron was obtained. Such an NLO polymer film can be used in electro-optic modulators.

Example 26

Chromophore III'-a

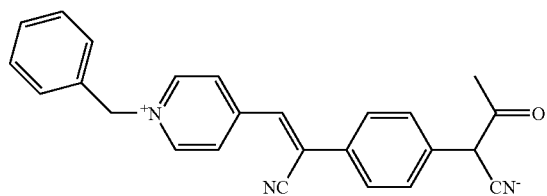

This compound is prepared in the similar way as described in Example 14, except that the reaction was done at room temperature. The yield was 44%. It absorbs at 590 nm (maximum peak) in DMF.

Example 27

Chromophore III'-b

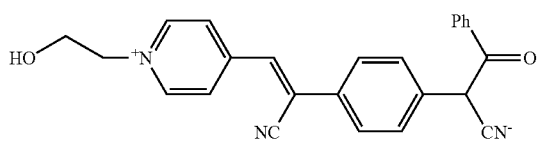

This compound is prepared in the similar way as described in Example 14, except that the reaction was done under reflux. No solid precipitated from the methanol solution during the reaction. The product was isolated after removal of solvent and passed through a short column packed with silica gel. The yield was 35%. It absorbs at 600 nm (maximum peak) in DMF.

Although the invention has been described with reference to specific embodiments, it will be evident to one skilled in the art that modifications can be made to these embodiments without departing from the spirit and scope of the invention. Accordingly, the invention is not to be limited to the specific embodiments disclosed, but is rather to be construed with respect to the attached claims, including obvious variations therefrom.

The invention claimed is:

1. Functionalized zwitterionic non-linear optical chromophores of structural formula III:

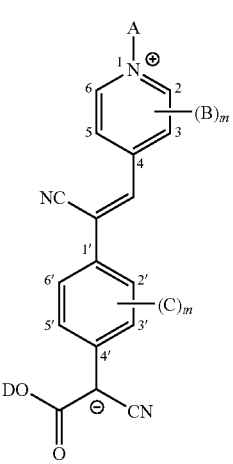

wherein

A is a linear or branched alkyl group having up to 20 carbon atoms and the desired functional groups, B is hydrogen, alkyl, aryl, halo, heterocyclic, alkoxy or nitro groups at 2, 3, 5 or 6 positions on the pyridine ring, C is hydrogen, aryl or a linear or branched alkyl group at 2', 3', 5' or 6' positions on the benzene ring, which has up to 70 carbon atoms and contains the desired functional group, D is a linear or branched alkyl, aryl or substituted aryl group, which has up to 70 carbon atoms and contains the desired functional group, and m is an integer of from 0 to 4.

2. A chromophore according to claim 1, wherein in A, the functional group is —OH (hydroxyl or phenolic), C≡CH, phenyl or $N_3$.

3. A chromophore according to claim 2, wherein B is hydrogen, at the 2, 3, 5 and 6 positions on the pyridine ring.

4. A chromophore according to claim 3, wherein C is hydrogen at the 2', 3', 5' and 6' positions.

5. A chromophore according to claim 3, wherein C is aryl.

6. A chromophore according to claim 1, wherein D is methyl, ethyl, 2-hydroxyethyl (—$CH_2CH_2OH$) and the derivatives of 2-hydroxyethyl (—$CH_2CH_2OR$), in which R is alkyl or alkoxycarbonyl having up to 50 carbon atoms with or without the presence of the functional group.

7. A chromophore according to claim 4, wherein D is —$CH_3$, —$CH_2CH_2OH$, —$CH_2C≡CH$, —$CH_2CH_2OCOCH_2N_3$ or

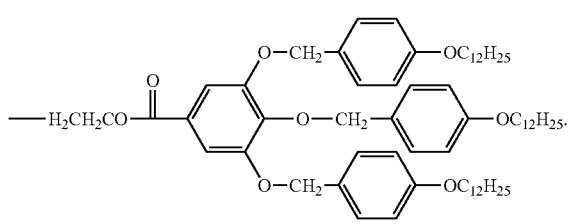

8. A chromophore according to claim 1, wherein B is hydrogen at the 2, 3, 5 and 6 positions on the pyridine ring, C is hydrogen at the 2', 3', 5' and 6' positions on the benzene ring, D is $CH_3$ and A is n-hexyl.

9. A chromophore according to claim 1, wherein B is hydrogen at the 2, 3, 5 and 6 positions on the pyridine ring, C is hydrogen at the 2', 3', 5' and 6' positions on the benzene ring, D is $CH_3$ and A is

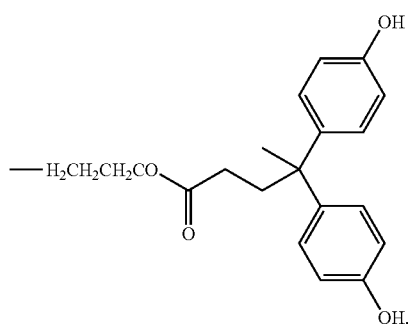

10. A chromophore according to claim 1, wherein B is hydrogen at the 2, 3, 5 and 6 positions on the pyridine ring, C is hydrogen at the 2', 3', 5' and 6' positions on the benzene ring, D is $CH_3$ and A is $CH_2CH_2OH$.

11. A chromophore according to claim 1, wherein B is hydrogen at the 2, 3, 5 and 6 positions on the pyridine ring, C is hydrogen at the 2', 3', 5' and 6' positions on the benzene ring, D is $CH_3$ and A is benzyl.

12. A chromophore according to claim 1, wherein B is hydrogen at the 2, 3, 5 and 6 positions on the pyridine ring, C is hydrogen at the 2', 3', 5' and 6' positions on the benzene ring, D is $CH_2CH_2OH$ and A is benzyl.

13. A chromophore according to claim 1 of structural formula

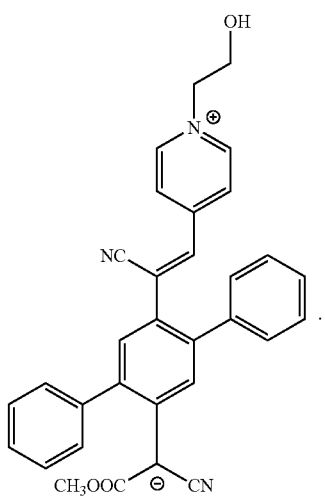

14. A chromophore according to claim 1 of structural formula

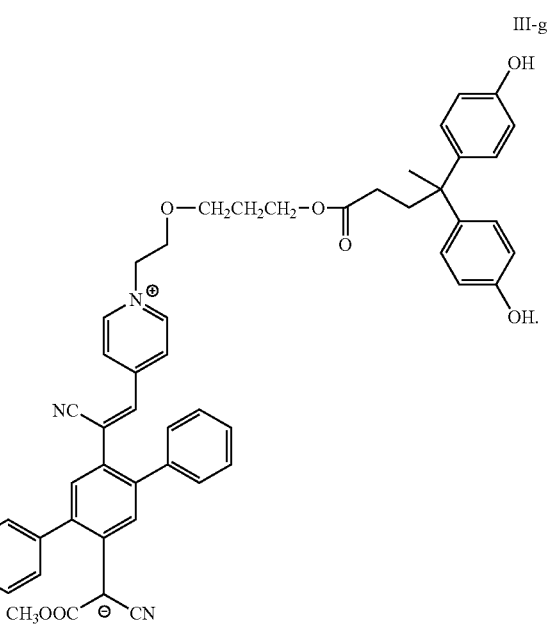

15. A process for making functionalized zwitterionic chromophores of structural formula III

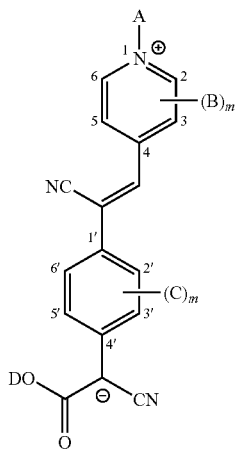

III wherein
A is a linear or branched alkyl group having up to 20 carbon atoms and the desired functional group, B is hydrogen, alkyl, aryl, halo, heterocyclic, alkoxy or nitro groups at 2, 3, 5 or 6 positions on the pyridine ring, C is hydrogen, aryl or a linear or branched alkyl group at 2', 3', 5' or 6' positions on the benzene ring, which has up to 70 carbon atoms and contains the desired functional group, D is a linear or branched alkyl, aryl or substituted aryl group, which has up to 70 carbon atoms and contains the desired functional group, and m is an integer from 0 to 4, comprising reacting a compound of formula I

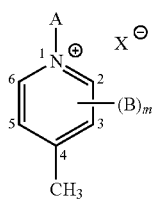

I wherein X is Cl, Br, I, tosylate or mesylate, with a compound of formula II

II in the presence of a base and a solvent.

16. A process according to claim 15, wherein the reaction is conducted at reflux temperatures, followed by UV-Vis.

17. A process according to claim 15, wherein the base is an amine or nitrogen heterocyclic.

18. A process according to claim 16, wherein the base is pyridine, quinoline, 1,8-diazabicyclo[5,4,0]undec-7-ene (DBU), 1,4-diazabicyclo[2,2,2]octane (DABCO), N-methyl piperidine, or N-(2-hydroxyethyl)piperidine.

19. A process according to claim 18, wherein the solvent is methanol, ethanol or acetonitrile.

20. A process according to claim 15, wherein D is methyl, ethyl, 2-hydroxyethyl (—CH$_2$CH$_2$OH) and the derivatives of 2-hydroxyethyl (—CH$_2$CH$_2$OR), in which R is alkyl and alkoxycarbonyl having up to 50 carbon atoms with or without the presence of the functional group.

21. A polymer comprising a host polymer and a chromophore of structural formula III as defined in claim 1.

22. A polymer according to claim 21, wherein the polymer is formed by mixing the host polymer and a chromophore of structural formula III, in an amount of 1-50% by weight.

23. A polymer according to claim 22, wherein the host polymer is a polysulfone.

24. A polymer according to claim 23, wherein the chromophore is of structural formula III wherein A is benzyl, B is hydrogen at the 2, 3, 5 and 6 positions, C is hydrogen at the 2', 3', 5' and 6' positions D is CH$_3$ and is present in an amount of 5-10% by weight.

25. A polymer according to claim 21, wherein the polymer is derived from the host polymer that is an acid-containing polysulfone and a chromophore of structural formula III, in an amount of 1-50 mole % relative to the host polymer.

26. A polymer according to claim 21, wherein a linear polymer is formed by condensation of a dihydroxy-containing chromophore of structural formula III and a diacid chloride.

27. A chromophore of structural formula
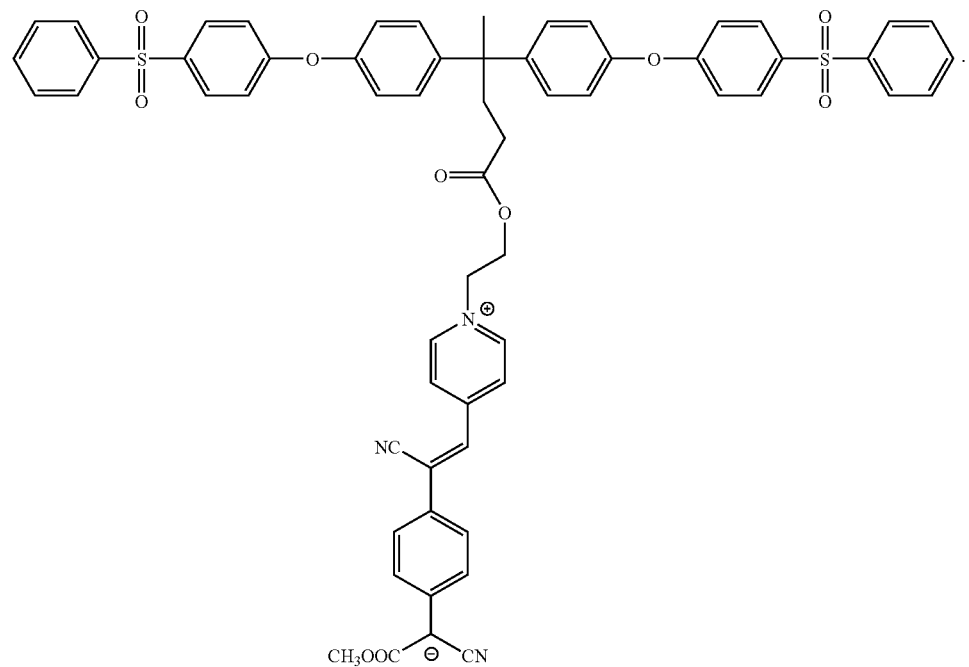
28. A chromophore according to claim 4, wherein D is $CH_3$ or $CH_2CH_2OH$.
29. A chromophore according to claim 4, wherein A is benzyl or $CH_2CH_2OH$.
* * * * *